US008383673B2

(12) United States Patent
Lau et al.

(10) Patent No.: US 8,383,673 B2
(45) Date of Patent: Feb. 26, 2013

(54) NITRIDOOSMIUM(VI) COMPLEXES FOR TREATMENT OF CANCER

(75) Inventors: Tai Chu Lau, Kowloon Tong (HK); Yun Wah Lam, Central (HK); Wai Lun Man, Sai Kung (HK); Wen Xiu Ni, Kowloon (HK); Chi-Ming Che, Midlevels West (HK)

(73) Assignees: City University of Hong Kong, Hong Kong (HK); Versitech Limited, Hong Kong (HK)

( * ) Notice: Subject to any disclaimer, the term of this patent is extended or adjusted under 35 U.S.C. 154(b) by 314 days.

(21) Appl. No.: 12/727,732

(22) Filed: Mar. 19, 2010

(65) Prior Publication Data

US 2011/0230456 A1    Sep. 22, 2011

(51) Int. Cl.
*A61K 31/555*    (2006.01)
*A61K 31/28*     (2006.01)
*C07D 231/56*    (2006.01)
*C07D 231/12*    (2006.01)
*C07C 251/24*    (2006.01)

(52) U.S. Cl. ........ 514/492; 514/186; 514/184; 548/108; 548/109; 556/137

(58) Field of Classification Search .................. 514/492, 514/186, 184; 548/108, 109; 556/137
See application file for complete search history.

(56) References Cited

U.S. PATENT DOCUMENTS 6,979,681 B2    12/2005    Morris et al.
7,338,946 B2    3/2008     Keppler
2004/0099529 A1    5/2004    Mao et al.

FOREIGN PATENT DOCUMENTS
WO    2008017855    2/2008

OTHER PUBLICATIONS

Luo et al. Cell, 2009, 136, pp. 823-837.*
Ni et al. Chem. Commun. 2011, 47, 2140-2142.*
Gura, Science Nov. 7, 1997: vol. 278. No. 5340, pp. 1041-1042.*
Leaf, Clifton, Health Administrator vol. XVII, No. 1: 172-183, 2005.*
"Expert Scientific Group on Phase One Clinical Trials Final Report" Nov. 30, 2006, pp. C1, C35-C38.*
Cancer Drug Design and Discovery Neidle, Stephen, ed. (Elsevier/Academic Press, 2008) p. 427.*
Kamb, Nature Reviews Drug Discovery 4, 161-165 (Feb. 2005).*
Ware DC, et al., Synthesis and reduction of osmium(VI) nitrido complexes and x-ray crystal structure of tetra-n-butylammonium octachlorodinitrido(m-pyrazine)diosmate(VI), Inorganic Chemistry (1991), 30(24), 4598-605.
Newton C, et al., Electron-Rich Nitrido-Bridged Complexes. Structure and Bonding in Triosmium Dinitrido Compounds, Inorganic Chemistry (1999), 38(18), 4032-4037.
Ware DC, et al., Substitution-induced nitrogen-nitrogen coupling for nitride coordinated to osmium(VI), Inorganic Chemistry (1991), 30(24), 4605-10.
Wright MJ, et al., Studies on transition-metal nitrido and oxo complexes. Part VII. Substituted nitrido complexes of osmium and ruthenium, Transition Metal Chemistry (Dordrecht, Netherlands) (1982), 7(1), 53-8.
Sen D, et al., Studies on nitrido complexes of osmium(VI) with N-heterocyclic bases, Indian Journal of Chemistry, Section A: Inorganic, Physical, Theoretical & Analytical (1978), 16A(10), 859-61.

* cited by examiner

*Primary Examiner* — Joseph Kosack
*Assistant Examiner* — Matthew Coughlin
(74) *Attorney, Agent, or Firm* — Heslin Rothenberg Farley & Mesiti P.C.

(57) ABSTRACT

The invention relates to nitridoosmium complexes and methods of using these compounds as treatments for cancer.

4 Claims, 1 Drawing Sheet

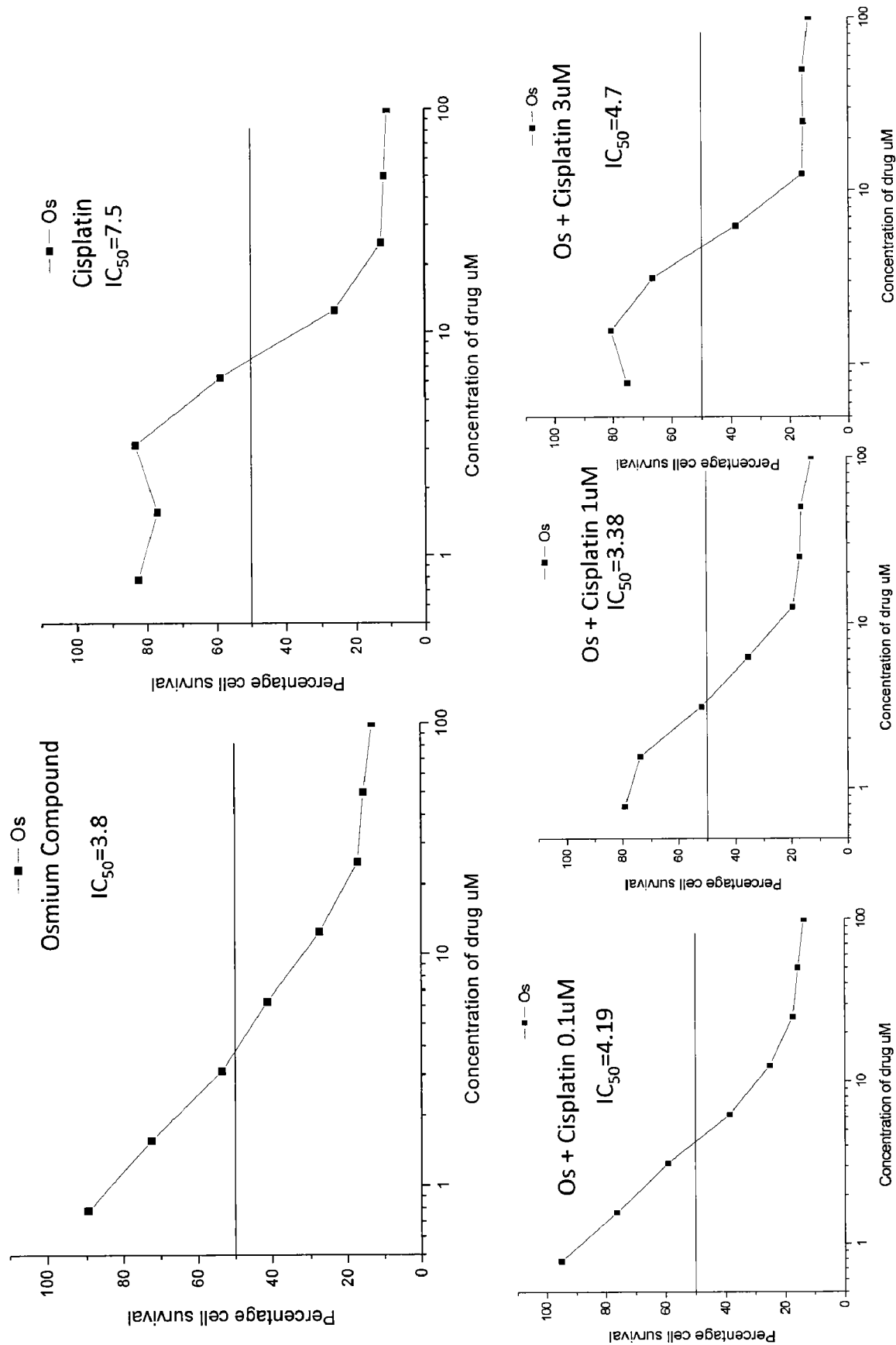

NITRIDOOSMIUM(VI) COMPLEXES FOR TREATMENT OF CANCER

FIELD OF THE INVENTION

The invention relates to nitridoosmium complexes that are useful as cancer treatments.

BACKGROUND OF THE INVENTION

Medicinal inorganic chemistry can exploit the unique properties of metal ions for the design of new drugs. The field of metal-based anticancer drugs was initiated by the platinum compound cisplatin, one of the leading agents in clinical use. Its importance is reflected by the fact that it is estimated that 50-70% of cancer patients are treated with metal-based drugs. However, cisplatin has some undesirable side effects and toxicities and, in addition, many solid tumors that initially respond to platinum-based therapy become resistant, and disease recurs. This has spurred chemists to employ different strategies in the development of new metal-based anticancer agents with different mechanisms of action.

Ruthenium compounds have been shown to have cytotoxic activity against human cancer cells. Some ruthenium complexes which have been shown to exhibit antitumor activity have been selected for clinical development as anticancer agents, specifically ($H_2$im)[trans-Ru$Cl_4$(imidazole)(DMSO)] (NAMI-A) and ($H_2$ind)[trans-Ru$Cl_4$(indazole)$_2$] (KP1019). These compounds also seem to have anti-metastatic activity.

Certain nitridoosmium(VI) complexes are known.

SUMMARY OF THE INVENTION

There exists a need for novel anticancer compounds which can be used as alternatives to the compounds which are currently available. The present invention provides a novel class of nitridoosmium complexes and methods of using them for their tumor inhibiting activity. These are potentially useful for the treatment of cancer.

In one aspect, the invention relates to a method of treating a proliferative disorder comprising administering to a patient in need of such treatment a therapeutically effective amount of at least one Os(VI) complex according to Formula I

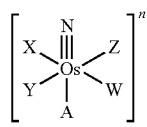

wherein
A, W, X, Y and Z are selected from electron donor ligands;
n is a negative, neutral or positive charge represented by −3, −2, −1, 0, +1, +2 or +3, respectively; and
wherein A, W, X, Y and Z may be optionally linked to each other in any combination.

In these cases, if none of A, W, X, Y or Z is a multidentate ligand, then at least one of W, X, Y and Z is a negatively charged electron donor ligand, and at least one of A, W, X, Y and Z is an optionally substituted heterocycle, other than imidazole or benzimidazole.

In another aspect, the invention relates to a compound of Formula II

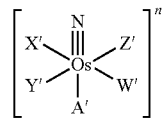

wherein
A', W', X', Y' and Z' are selected from electron donor ligands;
n is a negative, neutral or positive charge represented by −1, −2 −3, 0, +1, +2 or +3; and
wherein A', W', X', Y' and Z' may be optionally linked to each other in any combination.

In this aspect of the invention, at least one of W', X', Y' and Z' is halogen, water or hydroxyl. Additionally, if none of A', W', X', Y' and Z' forms a multidentate ligand, then at least one of A', W', X', Y' and Z' is optionally substituted pyrazole or indazole. Also, a multidentate ligand formed by any of A', W', X', Y' and Z' is selected from an imine, a diamine, 8-hydroxyquinoline, a glycol and oxalate.

In another aspect, the invention relates to a pharmaceutical composition comprising at least one compound of Formula I and a pharmaceutically acceptable carrier. In some of these aspects, the pharmaceutical composition comprises at least one compound of Formula I and at least one additional anticancer agent.

In another aspect, the invention relates to a pharmaceutical composition comprising at least one compound of Formula II and a pharmaceutically acceptable carrier. In some of these aspects, the pharmaceutical composition comprises at least one compound of Formula II and at least one additional anti-cancer agent.

BRIEF DESCRIPTION OF THE DRAWINGS

FIG. 1 depicts the results of the testing of a compound of the invention with and without cisplatin in the Microculture Tetrazolium Test (MTT) assay.

DETAILED DESCRIPTION OF THE INVENTION

Nitridoosmium compounds of the invention have been found to exhibit cytotoxic activity against several different types of cancer cell lines and can therefore be expected to show anticancer activity. Compounds of the invention may be effective in treating and/or preventing tumors caused by cells that are resistant to other cytotoxic drugs, such as cis-platin, for example.

An electron donor ligand refers to a ligand attached to the transition metal via a coordinative bond. The term negatively charged ligand is defined as a ligand in which the coordinating atom itself is negatively charged so that on coordination to a positively charged metal, the negative charge is neutralized. For example, a halide such as chloride or fluoride meets the present definition while a pyridine ligand bearing a negatively charged sulfonate group does not if the sulfonate group does not participate in coordination. Examples of negatively charged ligands include, but are not limited to, —F, —Cl, —Br, —I, —CN, —SCN, —OH, alkoxy, alkylthio and phenoxide. Examples of electron donor ligands include, but are not limited to, imine, water, halogen, amine, diamine, triamine, ammonia, alkyl, cyano, nitro, SCN, $NH_2$, $NH_3$, hydroxyl, alkoxy, phenoxy, oxalate, alcohol, alkylthio, thiol, thiolate, phosphite, β-diketone, alkylthio, phosphine, alkylnitrile, nitrite, nitrate, isocyanide, isocyanate, azide, a divalent sulfur-containing radical and optionally substituted heterocycle.

The suffix "dentate" refers to the number of linkages formed by a ligand with a central metal atom in a coordination complex. If one atom of the ligand binds to the metal atom, the ligand is monodentate. If two atoms of the ligand bind to the metal atom, the ligand is bidentate. If three atoms of the ligand bind to the metal atom, the ligand is tridentate. If four atoms of the ligand bind to the metal atom, the ligand is tetradentate (and so on). To illustrate, structure 1 below is a bidentate ligand (A and W are the same ligand, linked in two places to Os), and structure 2 below is a tetradentate ligand (Y, X, Z and W are all the same ligand, linked in four places to Os):

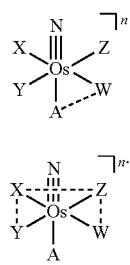

Note that in structure 1, A and W are part of the same single ligand, but are linked to the osmium atom in two places. For instance, the following compound could be a tridentate ligand, with links to the osmium at the nitrogen and at the two —OH groups:

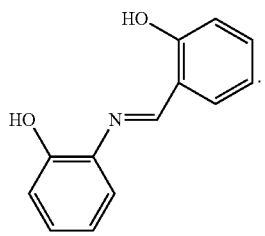 [SMILES: Oc1ccccc1/C=N/c1ccccc1O]

Similarly, in structure 2 above, Y, X, Z and W are all part of the same ligand, but are linked to the osmium atom in four places. One example of such a ligand is an amide of picolinic acid and a diamine, such as the N,N'-1,2-diaminocyclohexane-diylbis (2-pyridinecarboxamide) shown below:

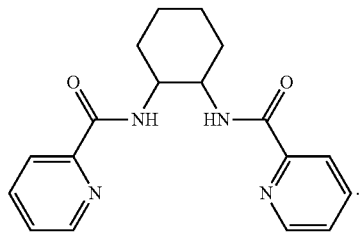 [SMILES: O=C(NC1CCCCC1NC(=O)c1ccccn1)c1ccccn1]

Water, halogen and hydroxyl might be viewed as monodentate ligands; however, in order to reduce confusion in this invention, unless otherwise specified, these three groups are not to be included in the definition of monodentate ligands. Suitable monodentate ligands, unless otherwise specifically indicated, may be represented by alkyl, cyano, nitro, SCN, $NH_2$, $NH_3$, phosphine, alkylnitrile, nitrite, nitrate, isocyanide, isocyanate, azide, alkoxy, phenoxy, alcohol, thiol, thiolate, phosphite, and optionally substituted heterocycle. Examples of other suitable monodentate ligands include, but are not limited to, alkylamine, dialkylamine, trialkylamine, diamine, imine (such as, but not limited to, a Schiff base), oxalate, glycol, alkylthio or heterocyclic compounds.

In some cases, a heterocycle may be substituted with one or more instances of lower alkyl, lower alkoxy, hydroxyl, alcohol, halogen, nitro, halo(lower)alkyl, $NH_2$ or cyano.

A bidentate ligand, in some instances, is an imine. In some cases, the imine is a Schiff base. In other instances, the bidentate ligand is a diamine. In some cases, the diamine may be ethylenediamine or propylenediamine. In yet other instances, the bidentate ligand is 8-hydroxyquinoline. In still other instances, the bidentate ligand is a glycol. In some cases, the glycol may be ethylene glycol or propylene glycol. In further instances, the bidentate ligand is picolinic acid. In other instances, the bidentate ligand is 2-hydroxypyridine. In yet other instances, the bidentate ligand is pyridine-2-thiol. In still other instances, the bidentate ligand is a β-diketone. In some cases, the β-diketone is acetylacetonate. In further instances, the bidentate ligand is oxalate.

A tridentate ligand is, in some aspects of the invention, an imine. In some cases, the imine is a Schiff base. For instance, the Schiff base may be N-salicylidene-2-aminophenol dianions. In other aspects, the tridentate ligand is a triamine. In still other aspects, the tridentate ligand is tris(1-pyrazolyl) borohydride anion or tris(1-pyrazolyl)methane. In yet other aspects, the tridentate ligand is 2,2':6',2"-terpyridine or 2,2': 6',2"-terpyrimidine. In further aspects, the tridentate ligand is a dicarboxylic acid of a nitrogen-containing heterocycle, wherein the carboxylic acids are adjacent to the nitrogen (for instance, pyridine-2,6-dicarboxylic acid). In still other aspects, the formulae shown below (formula IIIa and formula IIIb) may be mono-, bi- or tridentate ligands:

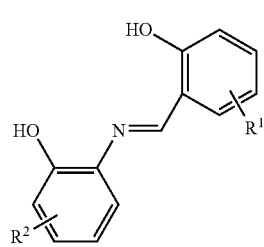

IIIa

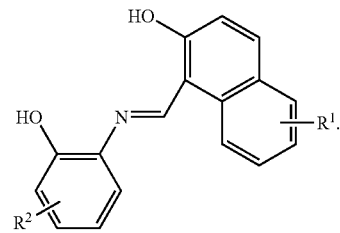

IIIb

In these formulae, $R^1$ and $R^2$ each represent one, two or three substituents and are each independently selected from hydrogen, halogen, lower alkyl, lower alkoxy, hydroxyl, nitro, $NH_2$ and cyano. In some of these substituents, $R^2$ is positioned para to the oxygen.

A tetradentate ligand is, in some instances of the invention, an amide of picolinic acid and a diamine, for instance, N,N'-1,2-diaminocyclohexane-diylbis(2-pyridinecarboxamide). In some instances, the tetradentate ligand may be an imine. As above, in some instances, the imine is a Schiff base. For instance, the tetradentate ligand may be the Schiff base of salicaldehyde and a diamine, such as those shown below:

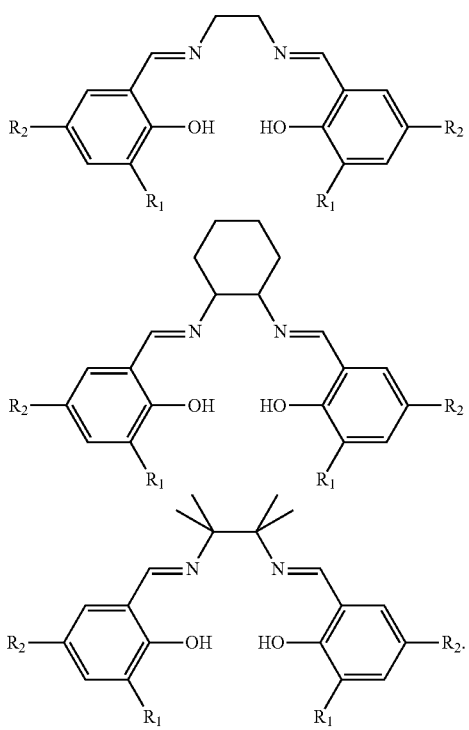

In these examples, $R^1$ can represent substituents such as (but not limited to) hydrogen, lower alkyl or halogen, and $R^2$ can be substituents such as (but not limited to) hydrogen, lower alkyl, halogen, nitro, or lower alkoxy.

In one aspect, the invention is method of treating a proliferative disorder comprising administering to a patient in need of such treatment a therapeutically effective amount of at least one complex according to Formula I

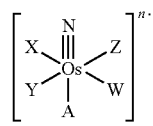

I

In some aspects of the invention, n is a negative charge represented by −3, −2, or −1. In other aspects of the invention, n is neutral, represented by 0. In still other aspects of the invention, n is a positive charge represented by +1, +2 or +3.

In some aspects, A, W, X, Y and Z are selected from electron donor ligands. A, W, X, Y and Z may be optionally linked to each other in any combination. If all of A, W, X, Y and Z are monodentate ligands (that is, none are linked to each other), then at least one of W, X, Y and Z is a negatively charged electron donor ligand, and at least one of A, W, X, Y and Z is optionally substituted heterocycle, but the heterocycle is not imidazole or benzimidazole.

In a subgenus of the invention, three of A, W, X, Y and Z are each independently halogen, water or hydroxyl and the remaining two of A, W, X, Y and Z are each monodentate ligands. In these instances, n is −2, −1 or 0. In one example, X, Y and Z are each independently chlorine, W is chlorine, pyrazole or indazole, and A is a pyrazole. In another example, A is an indazole. In some cases, the pyrazole and/or indazole is substituted with one or more instances of lower alkyl, lower alkoxy, hydroxyl, alcohol, halogen, nitro, halo(lower)alkyl, $NH_2$ or cyano. An illustrative compound of this subgenus is shown below:

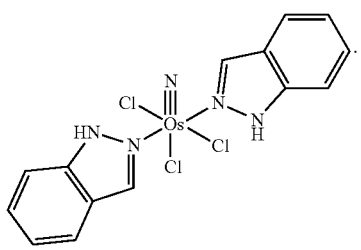

In another embodiment of this subgenus of the invention, three of A, W, X, Y and Z are each independently halogen, water or hydroxyl and the remaining two of A, W, X, Y and Z together form a bidentate ligand. In some members of this subgenus, X, Y and Z are each independently chlorine, and A and W together form a bidentate ligand selected from imine, a diamine, 8-hydroxyquinoline, a glycol, picolinic acid, 2-hydroxypyridine, pyridine-2-thiol, acetylacetonate and oxalate. One representative example is shown below:

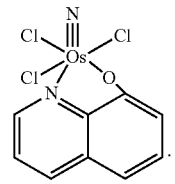

In another subgenus of the invention, two of A, W, X, Y and Z are each independently halogen, water or hydroxyl. In these instances, n is +1, 0, −1 or −2. In some embodiments of this subgenus, the remaining three of A, W, X, Y and Z each are monodentate ligands. In another aspect of this subgenus, one of the remaining A, W, X, Y and Z is a monodentate ligand, and the remaining two together form a bidentate ligand. In still another aspect of this subgenus, the remaining three of A, W, X, Y and Z together form a tridentate ligand, such as the representative example shown below:

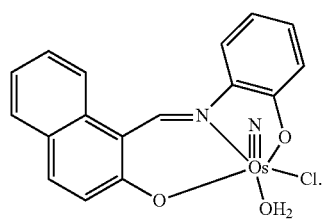

In another subgenus of the invention, one of A, W, X, Y and Z is halogen, water or hydroxyl. In these instances, n is +3, +2, +1, 0, −1 or −2. In some aspects of this subgenus, the remaining four of A, W, X, Y and Z each are monodentate ligands. In another aspect of this subgenus, one of the remaining A, W, X, Y and Z is a monodentate ligand, and the remaining three together form a tridentate ligand. In yet another aspect of this subgenus, two of the remaining A, W, X, Y and Z each are monodentate ligands, and the remaining two together form a bidentate ligand. In still another aspect of this subgenus of the invention, two of the remaining four of A, W, X, Y and Z together form a bidentate ligand, and the remaining two of A, W, X, Y and Z together form another bidentate ligand. In still another aspect of this subgenus of the invention, the remaining four of A, W, X, Y and Z together all form a tetradentate ligand, such as the representative example shown below:

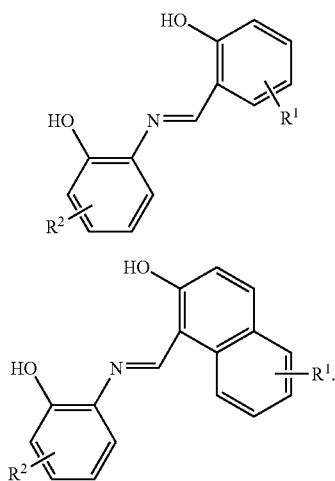

In one embodiment of the invention, n is 0, −1 or −2, and X, Y and Z are each independently chlorine. In some of these embodiments, A is selected from optionally substituted pyrazole and indazole and W is selected from chlorine and optionally substituted pyrazole or indazole. In other embodiments, A and W together form a bidentate ligand selected from imine, a diamine, 8-hydroxyquinoline, a glycol, picolinic acid, 2-hydroxypyridine, pyridine-2-thiol, acetylacetonate and oxalate. In some cases, the bidentate ligand is selected from a Schiff base, ethylenediamine, propylenediamine, ethylene glycol, propylene glycol, 8-hydroxyquinoline, picolinic acid, acetylacetonate and oxalate. In some of these embodiments, the ligand is selected from Formula IIIa and IIIb:

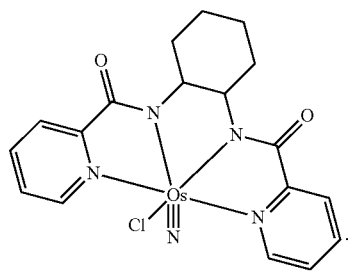

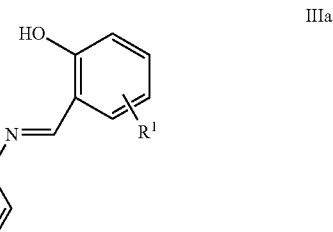

In these cases, $R^1$ and $R^2$ are each independently selected from hydrogen, chlorine, bromine, methyl, $NH_2$, methoxy, cyano and nitro, and $R^2$ is positioned para to the oxygen.

In one embodiment of the invention, n is +1, 0, −1 or −2; W is chlorine; Z is water or chlorine; and A, X and Y together form a tridentate ligand selected from an imine, triamine, tris(1-pyrazolyl)borohydride anion, tris(1-pyrazolyl)methane, 2,2':6',2''-terpyridine, 2,2':6',2''-terpyrimidine and a dicarboxylic acid of a nitrogen-containing heterocycle, wherein the carboxylic acids are adjacent to the nitrogen. In some of these embodiments, the ligand is selected from Formula IIIa and IIIb:

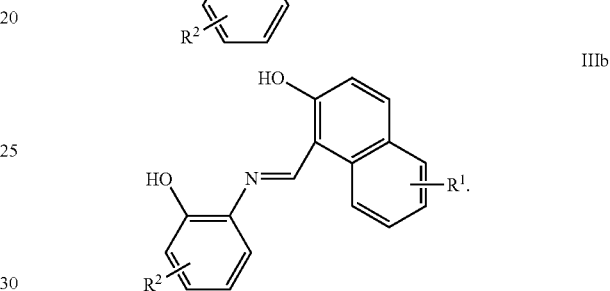

In these cases, $R^1$ and $R^2$ are each independently selected from hydrogen, chlorine, bromine, methyl, $NH_2$, methoxy, cyano and nitro, and $R^2$ is positioned para to the oxygen.

In one embodiment, the invention relates to a compound of Formula II

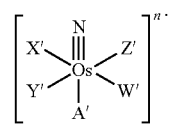

In some aspects of the invention, n is a negative charge represented by −3, −2, or −1. In other aspects of the invention, n is neutral, represented by 0. In still other aspects of the invention, n is a positive charge represented by +1, +2 or +3.

In some aspects, A', W', X', Y' and Z' are selected from electron donor ligands. A', W', X', Y' and Z' may be optionally linked to each other in any combination. At least one of A', W', X', Y' and Z' must be halogen, water or hydroxyl. Any multidentate ligand formed by any of A', W', X', Y' and Z' is selected from an imine, a diamine, 8-hydroxyquinoline, a glycol and oxalate. If all of A', W', X', Y' and Z' are monodentate ligands (that is, none are linked to each other), then at least one of A', W', X', Y' and Z' is optionally substituted pyrazole or indazole.

In a subgenus of the invention, three of A', W', X', Y' and Z' are each independently halogen, water or hydroxyl. In these instances, n is −2, −1 or 0. In one aspect of this subgenus, the remaining two of A', W', X', Y' and Z' are each monodentate ligands selected from cyano, nitro, SCN, $NH_2$, $NH_3$, phosphine, alkylnitrile, isocyanate, alkoxy, phenoxy, thiol, thiolate, phosphite, and optionally substituted pyrazole or indazole, at least one of which is optionally substituted pyrazole or indazole. In one example, X', Y' and Z' are each independently chlorine, W' is chlorine, pyrazole or indazole, and A' is a pyrazole. In another example, A' is an indazole. In some cases, the pyrazole and/or indazole is substituted with one or more instances of lower alkyl, lower alkoxy, hydroxyl, alcohol, halogen, nitro, halo(lower)alkyl, NH$_2$ or cyano. An illustrative compound of this subgenus is shown below:

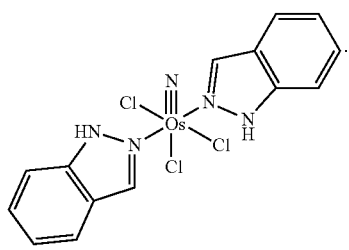

In another aspect of this subgenus of the invention, three of A', W', X', Y' and Z' are each independently halogen, water or hydroxyl and the remaining two of A', W', X', Y' and Z' together form a bidentate ligand selected from an imine, a diamine, 8-hydroxyquinoline, a glycol and oxalate. In some members of this subgenus, X', Y' and Z' are each independently chlorine, and A' and W' together form a bidentate ligand selected from an imine, a diamine, 8-hydroxyquinoline, a glycol and oxalate. One representative example is shown below:

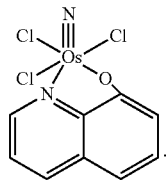

In another subgenus of the invention, two of A', W', X', Y' and Z' are each independently halogen, water or hydroxyl. In these instances, n is −2, −1, 0 or +1. In some aspects of this subgenus, the remaining three of A', W', X', Y' and Z' each are monodentate ligands, at least one of which is optionally substituted pyrazole or indazole. In another aspect of this subgenus, one of the remaining A', W', X', Y' and Z' is a monodentate ligand, and the remaining two together form a bidentate ligand selected from an imine, a diamine, 8-hydroxyquinoline, a glycol and oxalate. In still another aspect of this subgenus of the invention, the remaining three of A', W', X', Y' and Z' together form a tridentate ligand that is not 2,2':6',2''-terpyridine.

In another subgenus of the invention, one of A', W', X', Y' and Z' is halogen, water or hydroxyl. In these instances, n is −2, −1, 0, +1, +2 or +3. In some aspects of this subgenus, the remaining four of A', W', X', Y' and Z' each are monodentate ligands selected from cyano, nitro, SCN, NH$_2$, NH$_3$, phosphine, alkylnitrile, isocyanate, alkoxy, phenoxy, thiol, thiolate, phosphite, and optionally substituted pyrazole or indazole, at least one of which is optionally substituted pyrazole or indazole. In another aspect of this subgenus, one of the remaining A', W', X', Y' and Z' is a monodentate ligand selected from cyano, nitro, SCN, NH$_2$, NH$_3$, phosphine, alkylnitrile, isocyanate, alkoxy, phenoxy, thiol, thiolate, phosphite, and optionally substituted pyrazole or indazole, and the remaining three together form a tridentate ligand that is not 2,2':6',2''-terpyridine. In yet another aspect of this subgenus, two of the remaining A', W', X', Y' and Z' each are monodentate ligands selected from cyano, nitro, SCN, NH$_2$, NH$_3$, phosphine, alkylnitrile, isocyanate, alkoxy, phenoxy, thiol, thiolate, phosphite, and optionally substituted pyrazole or indazole, and the remaining two together form a bidentate ligand. In still another aspect of this subgenus of the invention, two of the remaining four of A', W', X', Y' and Z' together form a bidentate ligand, and the remaining two of A', W', X', Y' and Z' together form another bidentate ligand. In these aspects, the bidentate ligands may be an imine, a diamine, 8-hydroxyquinoline, a glycol and oxalate. In still another aspect of this subgenus of the invention, the remaining four of A', W', X', Y' and Z' together all form a tetradentate ligand.

In some embodiments of the invention, n is 0, −1 or −2 and X', Y' and Z' are each independently chlorine. In some of these embodiments, A' is selected from optionally substituted pyrazole and indazole and W' is selected from chlorine and optionally substituted pyrazole or indazole. In other embodiments, A' and W' together form a bidentate ligand selected from an imine, a diamine, 8-hydroxyquinoline, a glycol and oxalate. In some cases, the bidentate ligand is selected from a Schiff base, ethylenediamine, propylenediamine, ethylene glycol, propylene glycol, 8-hydroxyquinoline and oxalate. In some of these embodiments, the ligand is selected from Formula IIIa and IIIb:

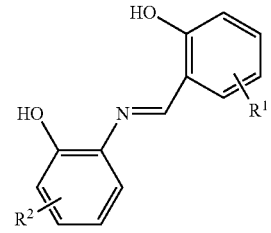

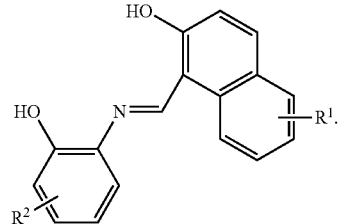

In these cases, R$^1$ and R$^2$ are each independently selected from hydrogen, chlorine, bromine, methyl, NH$_2$, methoxy, cyano and nitro, and R$^2$ is positioned para to the oxygen.

In one embodiment of the invention, n is +1, 0, −1 or −2; W' is chlorine; Z' is water or chlorine; and A', X' and Y' together form a tridentate imine ligand. In some of these embodiments, the ligand is selected from Formula IIIa and IIIb.

DEFINITIONS

Throughout this specification the terms and substituents retain their definitions.

Alkyl is intended to include linear, branched, or cyclic hydrocarbon structures and combinations thereof. A combination would be, for example, cyclopropylmethyl. Hydrocarbon refers to any substituent comprised of hydrogen and carbon as the only elemental constituents. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 or more carbon atoms. Examples of cycloalkyl groups include c-propyl, c-butyl, c-pentyl, norbornyl and the like.

Alkenyl refers to an unsaturated acyclic hydrocarbon radical in so much as it contains at least one double bond. Such radicals contain from 2 to 10 or more carbon atoms, preferably from 2 to 8 carbon atoms and more preferably 2 to 6 carbon atoms. Examples of suitable alkenyl radicals include propylenyl, buten-1-yl, isobutenyl, penten-1-yl, 2-methylbuten-1-yl, 3-methylbuten-1-yl, hexen-1-yl, hepten-1-yl, and octen-1-yl, alkadienes and the like.

Alkynyl refers to an unsaturated acyclic hydrocarbon radical in so much as it contains at least one triple bond. Such radicals contain from 2 to 10 or more carbon atoms, preferably from 2 to 8 carbon atoms and more preferably 2 to 6 carbon atoms. Examples of suitable alkynyl radicals include propynyl, butyn-1-yl, pentyn-1-yl, butyn-2-yl, 3-methylbutyn-1-yl, hexyn-1-yl, heptyn-1-yl, and octyn-1-yl and the like.

Alkoxy or alkoxyl refers to groups of from 1 to 8 or more carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower alkoxy refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, thiazole, furan, benzimidazole, quinoline, isoquinoline, quinoxaline, pyrimidine, pyrazine, tetrazole and pyrazole. As used herein aryl and heteroaryl refer to residues in which one or more rings are aromatic, but not all need be.

Heterocycle means a cycloalkyl or aryl carbocycle residue in which from one to three carbons is replaced by a heteroatom selected from the group consisting of N, O and S. The nitrogen and sulfur heteroatoms may optionally be oxidized, and a nitrogen heteroatom not directly attached to an osmium atom may optionally be quaternized. Unless otherwise specified, a heterocycle may be non-aromatic or aromatic. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, pyrazinyl, oxazolidinyl, isoxazolidinyl, thiazolidinyl, isothiazolyl, quinuclidinyl, isothiazolidinyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refers to alkyl, aryl, cycloalkyl, heterocyclyl, heterocyclyl, etc. wherein one or more H atoms in each residue are replaced with halogen, haloalkyl, alkyl, acyl, alkoxyalkyl, hydroxyloweralkyl, carbonyl, phenyl, heteroaryl, benzenesulfonyl, hydroxy, loweralkoxy, haloalkoxy, oxaalkyl, carboxy, alkoxycarbonyl [—C(=O)O-alkyl], alkoxycarbonylamino [HNC(=O)O-alkyl], carboxamido [—C(=O)NH$_2$], alkylaminocarbonyl [—C(=O)NH-alkyl], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2 or 3 hydrogen atoms are replaced with a specified radical. In the case of substituted hydrocarbon, more than three hydrogen atoms can be replaced by fluorine; indeed, all available hydrogen atoms could be replaced by fluorine. For purposes of this application, a metal-containing moiety is not to be an allowed substituent.

The language, "optionally substituted with one or more substituents selected from . . . " implies that a group could be substituted with one or more of one type of substituent or more than one type of substituent. For instance, the language, "aryl optionally substituted with one or more substituents selected from halogen and alkyl," indicates that the aryl could be substituted with, for instance (but not limited to) one chlorine; three chlorines; two chlorines and an ethyl; or one chlorine, two methyl groups and a fluorine.

The terms "haloalkyl" and "haloalkoxy" mean alkyl or alkoxy, respectively, substituted with one or more halogen atoms. The terms "alkylcarbonyl" and "alkoxycarbonyl" mean —C(=O)alkyl or —C(=O)—O-alkyl, respectively.

The term "halogen" means fluorine, chlorine, bromine or iodine. In one embodiment, halogen may be fluorine or chlorine.

"Phosphines" refer to a class of substituents containing a trivalent phosphorus atom having up to three substituents, —PR$^a$R$^b$R$^c$, wherein the R groups are hydrogen, lower alkyl or phenyl. Triphenylphosphine, trimethylphosphine or triethylphosphine are common phosphines.

An amine is any residue that contains one or more nitrogen(s), wherein the nitrogen is in the sp$^3$ configuration.

Alcohol refers to a residue containing one or more —OH groups.

An imine refers to a residue containing the structure —RR'C—N=R"—, wherein the R groups are generally carbon or hydrogen. The person of skill will understand that, for the purposes of this invention, an imine is not contained within a ring, except where the ring is formed due to the metal complex. To be absolutely clear, the —RR'C—N=R"— found within the ring of pyridine or pyrimidine is not an imine for purposes of this invention. The structure shown below, however, does contain an imine, even though rings are formed when the imine complexes with the metal atom:

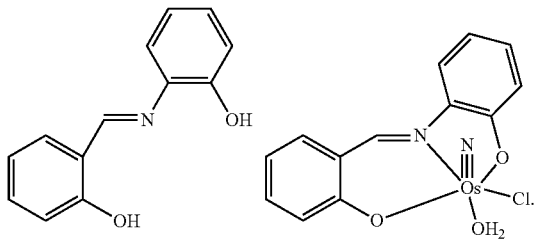

A Schiff base is a subset of imine with a formula of —RR'C=N—C— (i.e., R" is carbon, not hydrogen). Some Schiff bases of the invention include the N-salicylidene-2-aminophenol dianions (salpa) shown above or a Schiff base of salicaldehyde and a diamine, such as those shown below:

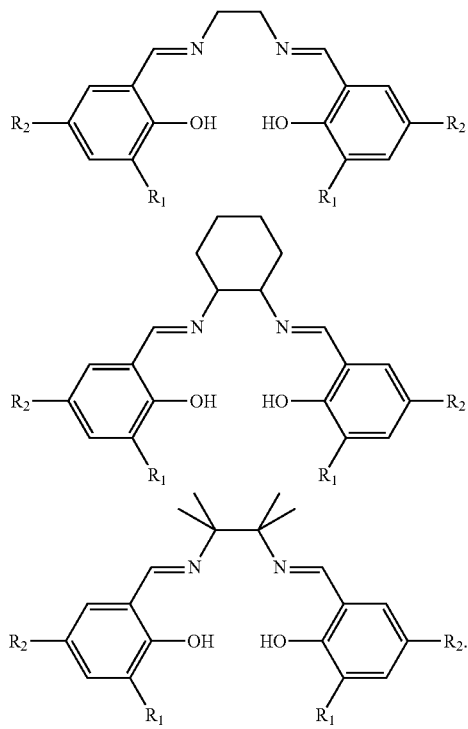

In these examples, $R^1$ can represent substituents such as (but not limited to) hydrogen, lower alkyl or halogen, and $R^2$ can be substituents such as (but not limited to) hydrogen, lower alkyl, halogen, nitro, or lower alkoxy.

In some instances of the invention, one or more of X, Y, Z, W and A and X', Y', Z', W' and A' may be a ligand that can only be monodentate, such as halogen. The person of skill will understand that these monodentate ligands will only be linked to the osmium and will not be part of a higher denticity substituent. To clarify, when the language states, "A, W, X, Y and Z may be optionally linked to each other in any combination," if Z is a halogen or water, it will not be additionally linked any of A, W, X or Y.

When referring to a substituent that can be a ligand, any hydrogen atoms on the moiety may or may not be present after complexing with the metal atom. For instance, reference to 8-hydroxyquinoline as a ligand choice is meant to indicate that, while 8-hydroxyquinoline is the stand-alone moiety, the hydrogens may not be present once the moiety is complexed with the metal atom (not all osmium bonds drawn below):

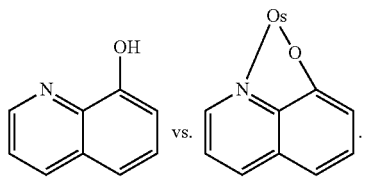

Similarly, a pyrazole ligand may be drawn in either of the ways shown below:

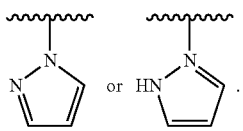

The total charge on the complex (n) will, however, change depending on the number of hydrogens that remain present.

The alkyl or aryl portions of any of the ligands are optionally substituted by —F, —Cl, —Br, —I, alkylamino, dialkylamino, trialkylammonium (except on aryl portions), alkoxy, alkylthio, aryl, or a reactive group. Any alkyl portions of the monodentate ligands generally contain 1 to 12 carbons. More typically, the alkyl portions contain 1 to 6 carbons. In other embodiments, the monodentate ligands are optionally substituted heterocyclic compounds containing at least one nitrogen, oxygen, or sulfur atom. Examples of suitable optionally substituted heterocyclic monodentate ligands include indazole, pyrazole, oxazole, thiazole, triazole, pyridine, isoxazole, isothiazole, oxadiazole, triazole, thiadiazole, pyran, pyridazine, pyrimidine, triazine, pyrazine, furan, thiophene, pyrrole, pyrroline, quinoline, isoquinoline, indole, indolizine, isoindole, benzofuran, benzothiophene, purine, phthalazine, quinazoline, quinoxaline, naphthyridine, phenazine, and the like, and derivatives thereof. For the purposes of this invention, when a heterocycle is attached to the osmium atom, it is attached at the heteroatom.

A "reactive group" is a functional group of a molecule that is capable of reacting with another compound to couple at least a portion of that other compound to the molecule. Reactive groups include carboxy, activated ester, sulfonyl halide, sulfonate ester, isocyanate, isothiocyanate, epoxide, aziridine, halide, aldehyde, ketone, amine, acrylamide, thiol, acyl azide, acyl halide, hydrazine, hydroxylamine, alkyl halide, imidazole, pyridine, phenol, alkyl sulfonate, halotriazine, imido ester, maleimide, hydrazide, hydroxy, and photo-reactive azido aryl groups. Activated esters, as understood in the art, generally include esters of succinimidyl, benzotriazolyl, or aryl substituted by electron-withdrawing groups such as sulfo, nitro, cyano, or halo groups; or carboxylic acids activated by carbodiimides.

Substituents R" are generally defined when introduced and retain that definition throughout the specification and in all independent claims.

While it may be possible for the compounds of formula I or formula II to be administered as the raw chemical, the compounds may also be presented as a pharmaceutical composition. According to a further aspect, the present invention provides a pharmaceutical composition comprising a compound of formula I or II, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The compounds of formula I or II are, by definition, going to be present as salts. The term "pharmaceutically acceptable salt" refers to salts prepared from pharmaceutically acceptable non-toxic acids or bases including inorganic acids and bases and organic acids and bases. When the compounds of the present invention are basic, salts may be prepared from pharmaceutically acceptable non-toxic acids including inorganic and organic acids. Suitable pharmaceutically acceptable acid addition salts for the compounds of the present invention include acetic, adipic, alginic, ascorbic, aspartic, benzenesulfonic (besylate), benzoic, boric, butyric, camphoric, camphorsulfonic, carbonic, citric, ethanedisulfonic, ethanesulfonic, ethylenediaminetetraacetic, formic, fumaric, glucoheptonic, gluconic, glutamic, hydrobromic, hydrochloric, hydroiodic, hydroxynaphthoic, isethionic, lactic, lactobionic, laurylsulfonic, maleic, malic, mandelic, methanesulfonic, mucic, naphthylenesulfonic, nitric, oleic, pamoic, pantothenic, phosphoric, pivalic, polygalacturonic, salicylic, stearic, succinic, sulfuric, tannic, tartaric acid, teoclatic, p-toluenesulfonic, and the like. When the compounds contain a net negative charge or an acidic side chain, suitable pharmaceutically acceptable base addition salts for the compounds of the present invention include, but are not limited to, metallic salts made from aluminum, calcium, lithium, magnesium, potassium, sodium and zinc or organic salts made from lysine, arginine, N,N'-dibenzylethylenediamine, chloroprocaine, choline, diethanolamine, ethylenediamine, meglumine (N-methylglucamine) and procaine. Further pharmaceutically acceptable salts include, when appropriate, nontoxic ammonium cations and carboxylate, sulfonate and phosphonate anions attached to alkyl having from 1 to 20 carbon atoms.

The compounds of the invention may be administered by a number of routes including, for example, orally, parenterally (including subcutaneous, intradermal, intramuscular, intravenous and intraarticular), rectally, topically (including dermal, buccal, sublingual and intraocular), nasally or via slow releasing microcarriers. The most suitable route may depend upon the condition and disorder of the recipient. The formulations may conveniently be presented in unit dosage form and may be prepared by any of the methods well known in the art of pharmacy. All methods include the step of bringing into association a compound of formula I or II or a pharmaceutically acceptable salt or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation. Thus, suitable carriers for use in the pharmaceutical compositions of the invention include saline, sterile water, creams, ointments, solutions, gels, pastes, emulsions, lotions, oils, solid carriers and aerosols.

Oral and parenteral sustained release drug delivery systems are well known to those skilled in the art, and general methods of achieving sustained release of orally or parenterally administered drugs are found in any standard pharmacy school textbook, for example *Remington: The Science and Practice of Pharmacy*. Chapter 94 of the 19th edition of Remington entitled "Sustained-Release Drug Delivery Systems" describes the more common types of oral and parenteral sustained-release dosage forms (pages 1660-1675.) The disclosure is incorporated herein by reference.

The compounds of the invention may be administered orally or via injection at a dose from 0.001 to 2500 mg/kg per day. The dose range for adult humans is generally from 0.005 mg to 10 g/day. The specific dosage level of the compounds and compositions of the invention will depend upon a number of factors, including the biological activity of the specific compound used and the age, body weight and sex of the subject. It will be appreciated that the subject may be a human or a mammalian animal.

The formulations include those suitable for oral, parenteral (including subcutaneous, intradermal, intramuscular, intravenous and intraarticular), rectal and topical (including dermal, buccal, sublingual and intraocular) administration.

The compounds and compositions of the invention can be administered alone or in combination with other compounds. The other compounds may have a biological activity which complements the activity of the compounds of the invention e.g., by enhancing its effect in killing tumors or by reducing any side-effects associated with the compounds of the invention.

As used herein, and as would be understood by the person of skill in the art, the recitation of "a compound"—unless expressly further limited—is intended to include salts, solvates and inclusion complexes of that compound as well as any stereoisomeric form, or a mixture of any such forms of that compound in any ratio. For purposes of this invention, "compound" and "complex" are interchangeable terms.

The term "tumor" is to be understood as referring to all forms of neoplastic cell growth, including tumors of the lung, liver, blood cells, skin, pancreas, stomach, colon, prostate, uterus, breast, lymph glands and bladder.

As used herein, reference to "treatment" of a patient is intended to include prophylaxis. The term "method of treating" when used in connection with these disorders means amelioration, prevention or relief from the symptoms and/or effects associated with these disorders.

The compounds of the invention may be used directly against a tumor. Alternatively or additionally, the compounds may be used to prevent or inhibit metastasis and/or to kill secondary tumors. It will be understood that the prevention or inhibition of metastasis is encompassed by the term "preventing cancer", as used herein.

Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Although this invention is susceptible to embodiment in many different forms, preferred embodiments of the invention are shown. It should be understood, however, that the present disclosure is to be considered as an exemplification of the principles of this invention and is not intended to limit the invention to the embodiments illustrated. It may be found upon examination that certain members of the claimed genus are not patentable to the inventors in this application. In this event, subsequent exclusions of species from the compass of applicants' claims are to be considered artifacts of patent prosecution and not reflective of the inventors' concept or description of their invention; the invention encompasses all of the members of the formulae I and II that are not already in the possession of the public.

ABBREVIATIONS

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations", is incorporated herein by reference. The following abbreviations and terms have the indicated meanings throughout:
ATCC=American Type Culture Collection
$^n$Bu=n-butyl
DMSO=dimethylsulfoxide
Et=ethyl
Me=methyl
nalph=1-[[(2-hydroxyphenyl)imino]methyl]-2-naphthalenol
PBS=phosphate buffered saline
py=pyridine
salpa=N-salicylidene-2-aminophenol dianions
SPF=specific pathogen free
Synthesis of Compounds The preparations of compounds used in this invention are shown in detail below. In general [$^n$Bu$_4$N][Os$^{VI}$(N)Cl$_4$] is reacted with the ligand in a suitable organic solvent, such as methanol, ethanol or dichloromethane. The Schiff base ligands 5-X—H$_2$salpa (salpa=N-salicylidene-2-aminophenol dianions) are synthesized by condensation of the appropriate 2-hydroxybenzaldehyde with the 2-aminophenol in refluxing ethanol. The Schiff base ligand nalph is synthesized by condensation of the 2-hydroxy-1-naphthaldehyde with the 2-aminophenol in refluxing ethanol. [N$^n$Bu$_4$][Os$^{VI}$(N)Cl$_4$] were prepared by a literature procedure (Griffith, W. P. and Pawson, D. J. *J. Chem. Soc., Dalton Trans.* 1973, 1315.).

Example 1

Synthesis of [Os$^{VI}$(N)(salpa)(OH$_2$)Cl]

1 equivalent of ligand H$_2$salpa (0.213 g, 1.0 mmol) was added to a solution of [$^n$Bu$_4$N][Os$^{VI}$(N)Cl$_4$] (0.588 g, 1.0 mmol) in methanol (30 mL) and the mixture was refluxed for 1 d. The resulting reddish orange precipitate was filtered off, washed with methanol (1 mL) and then air-dried. Yield: 69%. IR (KBr, cm$^{-1}$): ν(Os≡$^{14}$N) 1098, ν(Os≡$^{15}$N) 1063. Anal. Calcd. for C$_{13}$H$_{11}$N$_2$O$_3$ClOs: C, 33.30; H, 2.36; N, 5.97%. Found: C, 33.27; H, 2.47; N, 5.90%.

Example 2

Synthesis of [Os$^{VI}$(N)(5-Clsalpa)(OH$_2$)Cl]

The reddish orange solid was prepared by a procedure similar to that for [Os$^{VI}$(N)(salpa)(OH$_2$)Cl] using H$_2$5-Clsalpa. Yield: 55%. IR (KBr, cm$^{-1}$): ν(Os≡N) 1097. Anal. Calcd. for C$_{13}$H$_{10}$N$_2$O$_3$Cl$_2$Os: C, 31.02; H, 2.00; N, 5.57%. Found: C, 31.06; H, 2.26; N, 5.75%.

Example 3

Synthesis of [Os$^{VI}$(N)(5-Brsalpa)(OH$_2$)Cl]

The reddish orange solid was prepared by a procedure similar to that for [Os$^{VI}$(N)(salpa)(OH$_2$)Cl] using H$_2$5-Brsalpa. Yield: 62%. IR (KBr, cm$^{-1}$): ν(Os≡N) 1097. Anal. Calcd. for C$_{13}$H$_{10}$N$_2$O$_3$ClBrOs: C, 28.50; H, 1.84; N, 5.11%. Found: C, 28.77; H, 2.01; N, 5.15%.

Example 4

Synthesis of [Os$^{VI}$(N)(5-Mesalpa)(OH$_2$)Cl]

The reddish orange solid was prepared by a procedure similar to that for [Os$^{VI}$(N)(salpa)(OH$_2$)Cl] using H$_2$5-Mesalpa. Yield: 43%. IR (KBr, cm$^{-1}$): ν(Os≡N) 1092. Anal. Calcd. for C$_{14}$H$_{12}$N$_2$O$_3$ClOs: C, 34.89; H, 2.51; N, 5.81%. Found: C, 34.62; H, 2.88; N, 5.69%.

Example 5

Synthesis of [Os$^{VI}$(N)(5-MeOsalpa)(OH$_2$)Cl]

The reddish orange solid was prepared by a procedure similar to that for [Os$^{VI}$(N)(salpa)(OH$_2$)Cl] using H$_2$5-MeOsalpa. Yield: 45%. IR (KBr, cm$^{-1}$): ν(Os≡N) 1092. Anal. Calcd. for C$_{14}$H$_{12}$N$_2$O$_4$ClOs: C, 33.77; H, 2.43; N, 5.63%. Found: C, 33.67; H, 2.55; N, 5.39%.

Example 6

Synthesis of [Os$^{VI}$(N)(5-NO$_2$salpa)(OH$_2$)Cl]

The reddish orange solid was prepared by a procedure similar to that for [Os$^{VI}$(N)(salpa)(OH$_2$)Cl] using H$_2$5-NO$_2$salpa. Yield: 52%. IR (KBr, cm$^{-1}$): ν(Os≡N) 1097. Anal. Calcd. for C$_{13}$H$_{10}$N$_3$O$_5$ClOs: C, 30.38; H, 1.96; N, 8.18%. Found: C, 30.66; H, 1.94; N, 8.23%.

Example 7

Synthesis of [Os$^{VI}$(N)(nalph)(OH$_2$)Cl]

The red solid was prepared by a procedure similar to that [Os$^{VI}$(N)(salpa)(OH$_2$)Cl] using H$_2$nalph as ligand. Yield: 63%. IR (KBr, cm$^{-1}$): ν(Os≡N) 1097. Anal. Calcd. for C$_{17}$H$_{13}$N$_2$O$_3$ClOs: C, 39.35; H, 2.52; N, 5.40%. Found: C, 39.07; H, 2.55; N, 5.37%.

Example 8

Synthesis of [Os$^{VI}$(N)(pyrazole)$_2$Cl$_3$]

Pyrazole (95 mg, 1.4 mmol) was added to a solution of [$^n$Bu$_4$N][Os$^{VI}$(N)Cl$_4$] (200 mg, 0.34 mmol) in dichloromethane (10 ml) at room temperature. The solution was stirred for 16 h and the resulting pale orange solid was filtered, washed with a little CH$_2$Cl$_2$ followed by diethyl ether and air-dried. The compound was recrystallized by slow diffusion of diethyl ether into a methanol solution of the crude product. Yield: 43%. IR (KBr, cm$^{-1}$): ν(Os≡$^{14}$N) 1070, ν(Os≡$^{15}$N) 1036, ν(C≡N) 1484, ν(N—H) 3372; Anal. Calcd. for C$_6$H$_8$N$_5$Cl$_3$Os: C, 16.13; H, 1.80; N, 15.68%. Found: C, 16.43; H, 1.82; N, 15.59%. ESI-MS (acetone): m/z=+412, [Os$^{VI}$(N)(pyrazole)$_2$Cl$_2$$^+$].

Example 9

Synthesis of tran-[Os$^{VI}$(N)(indazole)$_2$Cl$_3$]

4 equivalent of ligand indazole (161 mg, 1.36 mmol) was added to a solution of ["Bu$_4$N][Os$^{VI}$(N)Cl$_4$] (200 mg, 0.34 mmol) in ethanol (10 mL) and the mixture was refluxed for 4 h. The resulting light brown precipitate was filtered off, washed with ethanol (1 mL) and diethyl ether, and then air-dried. Yield: 52%. Single crystals suitable for X-ray crystallography were obtained by slow diffusion of diethyl ether into the methanol solution of product. IR (KBr, cm$^{-1}$): ν(Os≡$^{14}$N) 1082, ν(Os≡$^{15}$N) 1041, ν(C═N) 1469, ν(N—H) 3289; Anal. Calcd. for C$_{13}$H$_{11}$N$_2$O$_3$ClOs: C, 30.75; H, 2.21; N, 12.81%. Found: C, 31.15; H, 2.29; N, 12.83%. ESI-MS (MeOH): m/z=+512, [Os$^{VI}$(N)(indazole)$_2$Cl$_2$$^+$].

Example 10

Synthesis of trans-[Os$^{VI}$(N)(3,5-dimethylpyrazole)$_2$Cl$_3$]

The purple-red powder was prepared by a procedure similar to that for [Os$^{VI}$(N)(pyrazole)$_2$Cl$_3$] using 3,5-dimethylpyrazole and 10 mL EtOH as solvent. Yield: 58%. IR (KBr, cm$^{-1}$): ν(Os≡N) 1075, ν(C═N) 1494, ν(N—H) 3235; Anal. Calcd. for C$_{10}$H$_{16}$N$_5$Cl$_3$Os: C, 23.89; H, 3.21; N, 13.93%. Found: C, 23.82; H, 3.25; N, 13.97%. ESI-MS (acetone): m/z=+468, [Os$^{VI}$(N)(3,5-dimethylpyrazole)$_2$Cl$_2$$^+$].

Example 11

Synthesis of trans-[Os$^{VI}$(N)(5-methylpyrazole)$_2$Cl$_3$]

To a solution of ["Bu$_4$N][Os$^{VI}$(N)Cl$_4$] (250 mg, 0.43 mmol) in 8 mL ethanol a 1.8 equivalent of 3-methylpyrazole (67 μL, 0.77 mmol) was added. After this mixture was stirred for 1 d, the solvent EtOH was evaporated to 0.5 mL and diethyl ether was added 20 ml). The resulting brick red solid was filtered off, washed with CH$_2$Cl$_2$ (1 mL) and diethyl ether, then air-dried. Yield: 76%. IR (KBr, cm$^{-1}$): ν(Os≡N) 1063, ν(C═N) 1497, ν(C—H) 3112, 3139, ν(N—H) 3225, 3318; Anal. Calcd. for C$_8$H$_{12}$N$_5$Cl$_3$Os: C, 20.24; H, 2.55; N, 14.75%. Found: C, 20.62; H, 2.57; N, 14.76%. ESI-MS (MeOH): m/z=+440, [Os$^{VI}$(N)(5-methylpyrazole)$_2$Cl$_2$$^+$].

Cytotoxicity Tests:

The cytotoxicity of the complexes was tested by using human cervix epitheloid carcinoma (HeLa) cell line. In this respect the following method was selected.

The antiproliferation activity of these nitridoosmium compounds was examined on human tumor cell lines in the Microculture Tetrazolium Test (MTT assay) with continuous active substance exposition (24 h for compound 1-7; 48 h for compound 8-11). In this regard, adherent monolayer cultures of HeLa cell line were used.

Culture conditions: The cells were kept in 10 cm$^2$ culture plates at 37° C. and moist atmosphere (5% CO$_2$). Dulbecco's Modified Eagle's Medium (DMEM) was used as culture medium, with 1% antibiotic-antimycotic and 10% fetal bovine serum.

Test execution: Cell were harvested from culture plates by trypsinization and seeded in 100 μL aliquots in complete culture medium into 96-well microculture plates. Cell density of about 4800 cells/well was chosen in order to ensure exponential growth throughout drug exposure. Cells were allowed to settle for 24 h, followed by the addition of dilutions of the test compounds, which were dissolved in DMSO, in 100 μL/well complete culture medium (<1% DMSO) and incubation for 24 h (compound 1-7) or 48 h (compound 8-11). At the end of exposure, drug solutions were replaced by 100 μL/well DMEM medium with 10% MTT solution in phosphate-buffered saline (5 mg/ml PBS). After incubation for 1 h at 37° C., medium was removed, and the reduced formazan product formed by the metabolic activity of vital cells was dissolved in 100 μL DMSO per well. Optical densities at a wavelength of 570 nm were measured with a microplate reader. The quantity of vital cells was expressed in terms of T/C values by comparison to untreated control microcultures, and IC$_{50}$ values were calculated from concentration-effect curves by logarithmic interpolation. Evaluation is based on means from at least three independent experiments, each comprising four replicates per concentration level.

TABLE

Cytotoxicity of Nitridoosmium Complexes in HeLa Cell Line

| Compound (Example No.) | IC$_{50}$ (μM)* |
|---|---|
| 1 | A |
| 2 | A |
| 3 | A |
| 4 | A |
| 5 | A |
| 6 | B |
| 7 | A |
| 8 | A |
| 9 | A |
| 10 | B |
| 11 | B |

*IC$_{50}$ Values: A is <25 μM; B is <100 μM

In Vitro Tests

In vitro cultured human non-small cell lung cancer cells NCI-H460 (from ATCC) were inoculated in nude mice (SPF grade BALB/c-nu male nude mice were purchased from Medical Laboratory Animal Center, Guangdong Province) subcutaneously. The in vivo anti-cancer properties of Os1 (Compound 8) and Os2 (Compound 1) given by intraperitoneal injection were examined by measuring the tumor nodule size of the nude mice.

Each nude mouse was inoculated subcutaneously with 0.2 mL of 7.5×10$^6$ cells/mL of NCI-H460 cells suspended in culture medium. Tumor nodules on nude mice were observed nine days after inoculation and injections of Os1, Os2, cyclophosphamide (positive control) and 20% PET solution[1] (negative control) were performed on that day. In terms of tumor volume, there is a significant different between the positive control group and the negative control group 18, 22, 26 and 30 days after treatment. There is also a significant different in tumor volume between the treatment group of Os2 (1 mg/kg) and that of the negative control 30 days after treatment.

[1] 20% PET solution=(Polyethylene glycol 400, 12%; ethanol 6%; Tween 80, 2% and PBS 80%)

Materials: Os1 and Os2 were prepared by City University of Hong Kong, Hong Kong. Disposable sterile 1 ml syringe; vernier caliper (No. 01,000,101 River system, GB/T1214.2)

Chengdu Measuring & Cutting Tool Co., Ltd. production; Tecniplast separately ventilated cage (Italy), ultra-clean bench.

Experimental Conditions: SPF grade animal laboratories equipped with independent ventilated cages (qualified number: 2006C021). Laboratory animal permission number: SCXK (Guangdong) 2008-0002. Temperature: 22-26° C., humidity: 40-70%, 12 h light- and dark-switched alternately. Independent ventilation cage with maximum wind speed of 35 m$^3$/h and actual wind speed of 20 m$^3$/h. Each nude mouse was cultured in separated breeding cage.

Experimental Procedure: 16-18 g male BALB/c-nu nude mice were inoculated subcutaneously 0.2 mL of the NCI-H460 cell suspension ($1.5 \times 10^6$ cells/rats). The day after inoculation (administration day 1), the nude mice were randomly divided into eight groups and were grouped as follows:

1) positive group (cyclophosphamide 30.0 mg/kg, intraperitoneal injection)

2) negative group (20% PET, intraperitoneal injection)

3) Os1 groups (three treatment groups: 10, 3, 1 mg/kg, intraperitoneal injection)

4) Os2 groups (three treatment groups: 10, 3, 1 mg/kg, intraperitoneal injection)

Mice in each group were received treatment twice a week, with a total number of eight injections. Tumor sizes were measured every 3 days. The treated mice were sacrificed at the end of the study period (30 days) with anatomical separation of tumor nodules. The tumors were weighed and photographed.

The inhibition rate of tumor growth was determined using the following formula:

Tumor growth inhibition rate (%)=(1−mean tumor weight of the treatment/mean tumor weight of the negative group)×100%. Tumor volume=longest dimension (mm)×[shortest dimension of the tumor (mm)]$^2$/2. All measurements were expressed in Mean±SD, using SPSS 10.0 for statistical analysis.

Results: In the Os2 high-dose group, one treated mouse died at day 7 and one died at day 19. In the Os2 middle dose group one treated mouse died at day 23 and one died at day 26. Nine days after inoculation of the cancer cells, tumors were observed in each mouse. Table 1 shows the tumor weight and Table 2 depicts the tumor volume.

TABLE 1

Tumor size measurement (Mean ± SD)

| group | number of mice | dose/ mg·kg$^{-1}$ | tumor weight (g) | inhibition rate (%) |
|---|---|---|---|---|
| negative control | 5 | — | 2.3482 ± 1.0455 | — |
| positive control | 5 | 30.0 | 0.6095 ± 0.5477* | 74.04 |
| Os1 low dose | 5 | 1 | 1.7206 ± 0.4289 | 26.73 |
| Os1 medium dose | 5 | 3 | 2.0631 ± 1.1693 | 12.14 |
| Os1 high dose | 5 | 10 | 2.7711 ± 1.0732 | −18.01 |
| Os2 low dose | 5 | 1 | 1.2164 ± 0.6547 | 48.20 |
| Os2 medium dose | 5 | 3 | 1.3542 ± 0.5337 | 42.33 |
| Os2 high dose | 5 | 10 | 2.1535 ± 1.4884 | 8.29 |

Compared with negative control: *P < 0.05

TABLE 2

Tumor volume (Mean ± SD)

| group | dose/ mg·kg$^{-1}$ | number of mice | Tumor volume/mm$^3$ | | | | |
|---|---|---|---|---|---|---|---|
| | | | day 14 | day 18 | day 22 | day 26 | day 30 |
| −ve | — | 5 | 405.5 ± 191.11 | 834.70 ± 383.67 | 1207.93 ± 722.09 | 1952.96 ± 1294.35 | 2590.19 ± 1638.80 |
| +ve | 30 | 5 | 168.16 ± 117.68 | 227.03 ± 167.96* | 318.64 ± 334.09* | 378.31 ± 233.53* | 778.84 ± 574.55* |
| Os1 low dose | 1 | 5 | 288.12 ± 87.38 | 518.99 ± 241.97 | 801.59 ± 422.76 | 1319.35 ± 748.80 | 1569.69 ± 557.16 |
| Os1 medium dose | 3 | 5 | 482.89 ± 298.61 | 1043.37 ± 679.42 | 1140.42 ± 675.13 | 1537.35 ± 967.22 | 2262.38 ± 868.18 |
| Os1 high dose | 10 | 5 | 534.98 ± 236.90 | 901.64 ± 313.88 | 1422.37 ± 581.23 | 2004.80 ± 717.39 | 2511.59 ± 1011.51 |
| Os2 low dose | 1 | 5 | 380.21 ± 302.43 | 710.06 ± 669.55 | 726.71 ± 754.02 | 1365.02 ± 1222.89 | 1110.38 ± 541.57* |
| Os2 medium dose | 3 | 5 | 420.80 ± 405.23 | 500.45 ± 286.63 | 1011.29 ± 200.62 | 1032.38 ± 495.14 | 1390.62 ± 571.16 |
| Os2 high dose | 10 | 5 | 507.33 ± 411.74 | 671.87 ± 449.98 | 1342.17 ± 1176.17 | 1601.47 ± 1286.31 | 2188.17 ± 1724.71 |

Compared with negative control group: *P < 0.05

MTT Assay:

Compound 8 was tested in the MTT assay to determine its effects with and without cisplatin (see FIG. 1). Assays of cytotoxicity were conducted in 96-well, flat-bottomed microtitre plates. The supplemented culture medium (MEM, 40 μL) with HeLa cells ($1 \times 10^5$ cells per mL) was added to the wells. Compound 8 was dissolved in the culture medium with 0.5% DMSO with concentrations ranged from 5 μM to 100 μM, and aliquots (10 μL) of the solutions were subsequently added to a set of wells containing the HeLa cells. To examine the synergistic effect of cisplatin, cisplatin was dissolved in the culture medium in order to prepare solutions with concentrations of 0, 0.2, 2 and 6 μM. Aliquots of the cisplatin solutions (50 μL) were added to different sets of the wells containing compound 8 and the HeLa cells. Cells for control experiments were treated with supplemented media with 0.5% DMSO (100 μL). The microtitre plates were incubated at 37° C. in a humidified atmosphere of 5% CO$_2$/95% air for a further 3 days. Assessment of cytotoxicity was carried out by using a modified method of the Mosmann-based 3-(4,5-dimethylthiazol-2-yl)-2,5-diphenyltetrazolium bromide (MTT) assay [T. Mosmann, *J. Immunol. Methods* 1983, 65, 55]. At the end of the incubation period, MTT solution (10 μL, Cell Proliferation Kit I, Roche) was added into each well and the cultures were incubated further for 4 h at 37° C. in a humidified atmosphere of 5% $CO_2$/95% air. A solubilizing solution (100 μL) was added into wells to lyse the cells and to solubilize the formed formazan complex. The microtitre plates were maintained in a dark, humidified chamber overnight. The formation of formazan was measured by using a microtitre plate reader at 550 nm and the percentages of cell survival were determined. The cytotoxicity was evaluated based on the percentage cell survival in a dose-dependent manner relative to the control. Table 3 below summarizes the results:

TABLE 3

Results of MTT Assay

| Compound 8 | Cisplatin (concentration) | $IC_{50}$ (in μM) |
|---|---|---|
| Yes | None | 3.8 |
| Yes | 0.1 μM | 4.19 |
| Yes | 1.0 μM | 3.38 |
| Yes | 3.0 μM | 4.7 |
| None | 0.5-100 μM μM | 7.5 |

In short, Compound 8 is more effective than cisplatin in the MTT assay. Further, the presence of cisplatin does not provide any synergistic effect when administered with Compound 8.

The invention claimed is:

1. A method of treating a proliferative disorder comprising administering to a patient that has said disorder a therapeutically effective amount of at least one complex according to Formula I

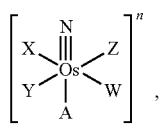

wherein
n is 0, −1 or −2;
two of A, W, X, Y and Z are each independently selected from optionally substituted pyrazole and indazole; and
the remaining three of A, W, X, Y and Z are each independently chlorine;
wherein said disorder is selected from human cervix epithelioid carcinoma, non-small cell lung cancer, liver cancer, blood cell cancer, and lung cancer.

2. A method according to claim 1, wherein said complex is selected from

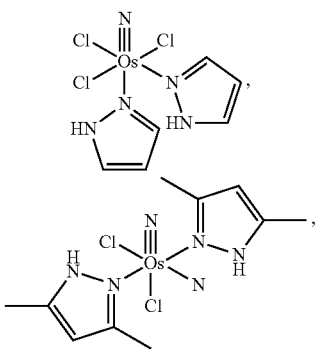

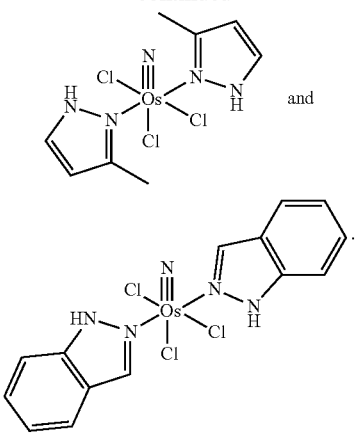

3. A method of treating a proliferative disorder comprising administering to a patient that has said disorder a therapeutically effective amount of at least one complex according to Formula I

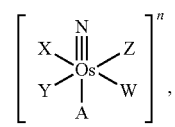

wherein
n is 0, −1 or −2; and
a) X, Y and Z are chlorine; and A and W form together a bidentate ligand selected from Formula IIIa and IIIb:

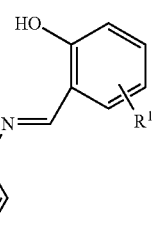

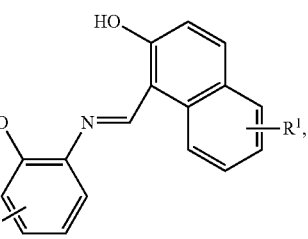

wherein $R^1$ and $R^2$ are each independently selected from hydrogen, chlorine, bromine, methyl, $NH_2$, methoxy, cyano and nitro, and $R^2$ is positioned para to the oxygen; or b) W is chlorine; Z is water or chlorine; and A, X and Y form a tridentate ligand selected from Formula IIIa and IIIb:

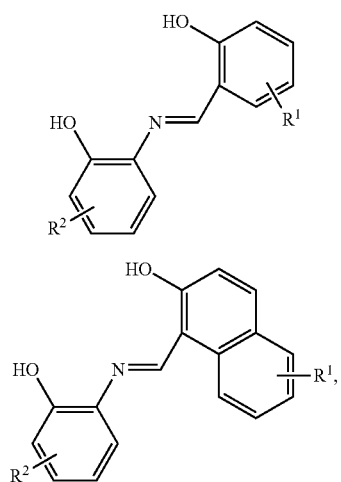

wherein $R^1$ and $R^2$ are each independently selected from hydrogen, chlorine, bromine, methyl, $NH_2$, methoxy, cyano and nitro, and $R^2$ is positioned para to the oxygen; wherein said disorder is selected from human cervix epithelioid carcinoma, non-small cell lung cancer, liver cancer, blood cell cancer, and lung cancer.

4. A method according to claim 3, wherein said complex is selected from

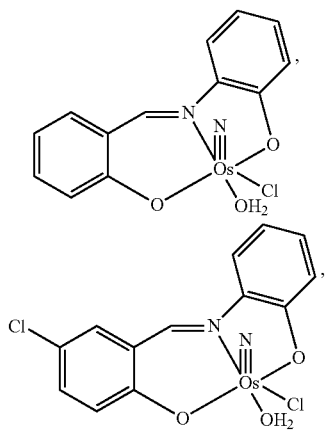

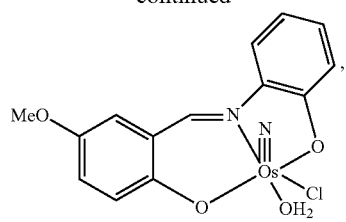

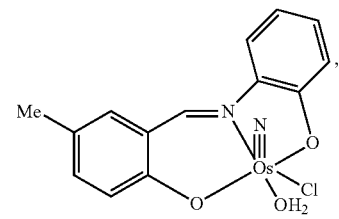

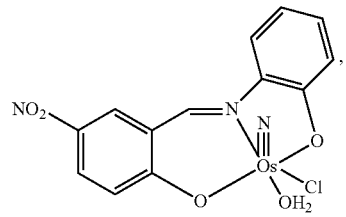

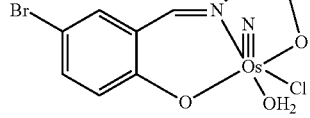

, and

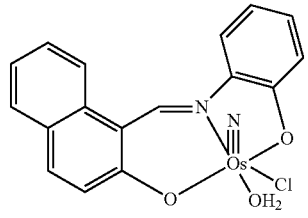

.

* * * * *